United States Patent [19]
McHardy et al.

[11] Patent Number: 5,481,181
[45] Date of Patent: Jan. 2, 1996

[54] REAL-TIME TOXIC METALS MONITOR DEVICE AND METHOD

[75] Inventors: John McHardy, Westlake Village; Carl W. Townsend, Los Angeles; Clifford A. Megerle, Thousand Oaks, all of Calif.

[73] Assignee: Hughes Aircraft Company, Los Angeles, Calif.

[21] Appl. No.: 283,457

[22] Filed: Aug. 1, 1994

[51] Int. Cl.⁶ .................................................. G01N 27/42
[52] U.S. Cl. ..................... 324/71.1; 324/425; 204/153.1; 204/412; 204/431
[58] Field of Search .................................. 324/71.1, 425; 204/153.1, 400, 412, 431, 432

[56] References Cited

U.S. PATENT DOCUMENTS

| | | | |
|---|---|---|---|
| 3,713,994 | 1/1973 | Shults et al. | 204/412 X |
| 3,909,384 | 9/1975 | Jasinski et al. | 204/412 |
| 3,929,587 | 12/1975 | Gallagher | 204/412 X |
| 3,969,209 | 7/1976 | Mueller | 204/412 X |
| 4,581,122 | 4/1986 | Hammond et al. | 204/412 |
| 4,587,003 | 5/1986 | Tantram et al. | 204/412 |
| 4,769,122 | 9/1988 | Marrese et al. | 204/412 X |
| 5,302,274 | 4/1994 | Tomantschger et al. | 204/412 |
| 5,316,648 | 5/1994 | Kühn et al. | 204/412 X |

OTHER PUBLICATIONS

J. Giner, "The structure of hydrophobic gas diffusion electrodes", in *From Electrocatalysis to Fuel Cells*, G. Sandstede, Ed., University of Washington Press, Seattle, Wash., pp. 215–222 (1972).

S. Trasatti, "Development of the work function approach to the underpotential deposition of metals: application to the hydrogen evolution reaction", *Zeitschrift für Physikalische Chemie Neue Folge*, Bd. 98, S. 75–94 (1975).

*Primary Examiner*—Kenneth A. Wieder
*Assistant Examiner*—Diep Do
*Attorney, Agent, or Firm*—M. E. Lachman; M. W. Sales; W. K. Denson-Low

[57] ABSTRACT

An device for monitoring workplace air comprises a monitor cell comprising a base and a removable assembly. The removable assembly comprises (1) a flat, electrically insulating substrate having a first surface, (2) an electrolyte cell having an anode and a cathode disposed on the first surface, the anode and cathode spaced apart to define a controlled volume for holding a quantity of an electrolyte, and (3) means for applying a controlled electrical potential to the cathode. The base comprises (1) an air inlet portion for sampling air, (2) an air outlet portion connected to an air sampling pump, (3) a channel connecting the air inlet and the air outlet and adapted to introduce air to the electrolyte in the electrolyte cell, (4) a reservoir for storing the electrolyte for the electrolyte cell, and (5) a wick for supplying electrolyte from the reservoir to the electrolyte cell.

19 Claims, 3 Drawing Sheets

REAL-TIME TOXIC METALS MONITOR DEVICE AND METHOD

BACKGROUND OF THE INVENTION

1. Field of the Invention

The present invention relates to an improved device and method for monitoring the presence of toxic metals in workplace air, and more particularly, to real-time detection of such toxic metals.

2. Description of Related Art

Toxic metals have a negative impact on human health. The term toxic metals is used herein to include hazardous, inorganic species, such as cadmium, lead, mercury, and thallium and their soluble compounds. These compounds include any oxides, chlorides, acetates, nitrates, perchlorates, phosphates, and other salts that can be dissolved in water or in acidic solutions. The use of toxic metals in the workplace necessitates stringent precautions against accidental release. The Occupational Safety and Health Agency (OSHA) has recently reduced the permissible exposure limit of personnel to airborne cadmium particles to 5.0 micrograms/cubic meter and stipulated an action level for airborne cadmium particles at 2.5 micrograms/cubic meter. Corporations are now faced with a significant liability associated with the exposure of personnel to these materials.

At present, the most commonly used personnel monitors rely upon adsorbent or absorbent tubes and miniature air sampling pumps, followed by laboratory chemical analysis of compounds collected over long periods of time. Organizations that do not have in-house laboratories must often wait days for these analytical results. The detection limits of many of these monitors often lack the sensitivity required by OSHA and suffer from interferences that are difficult or impossible to resolve.

Prior personnel monitors for cadmium require the collection filter from a personnel air sampling pump to be sent to an off-site laboratory for analysis by skilled chemical technicians. Results of these tests are not available for several days. Personnel may experience multiple days of cadmium exposure before corrective action can be taken.

Thus, a need exists for a sensitive, real-time monitor for toxic metals such as those listed above, with detection limits that meet the new, lower OSHA exposure limits for toxic metals, to safeguard both workers and the environment.

SUMMARY OF THE INVENTION

In accordance with the invention, an improved device is provided for monitoring the presence of toxic metals in workplace air. The device comprises a monitor cell comprising a base and a removable assembly. The removable assembly comprises (1) a flat, electrically insulating substrate having a first surface, (2) an electrolyte cell having an anode and a cathode disposed on the first surface, the anode and cathode spaced apart to define a controlled volume for holding a quantity of an electrolyte, and (3) means for applying a controlled electrical potential to the cathode of the electrolyte cell. The base comprises (1) an air inlet portion for sampling air, (2) an air outlet portion connected to an air sampling pump, (3) a channel connecting the air inlet and the air outlet and adapted to introduce the air to the electrolyte in the electrolyte cell, (4) a reservoir for storing electrolyte for the electrolyte cell, and (5) a wick for supplying electrolyte from the reservoir to the electrolyte cell.

The present invention discloses a device for real-time monitoring of toxic metals such as cadmium, and lead in workplace air.

The device of the present invention will detect when workers have been exposed to concentrations of toxic metals greater than that allowed by OSHA requirements. Rather than waiting several-days for off-site testing, the test results from the present invention are evaluated in real-time. If high levels of toxic metals such as cadmium and lead are detected, immediate action can be taken to identify the source and apply remedial action. If necessary, the worker can be treated for toxic metal overdose immediately.

BRIEF DESCRIPTION OF THE DRAWINGS

FIG. 4a) and of current (milliamps; FIG. 4b) both with respect to time, show the applied voltage and hydrogen evolution current, respectively, as a function of time associated with the detection of lead in the presence of cadmium.

DESCRIPTION OF THE PREFERRED EMBODIMENTS

Figure 1:
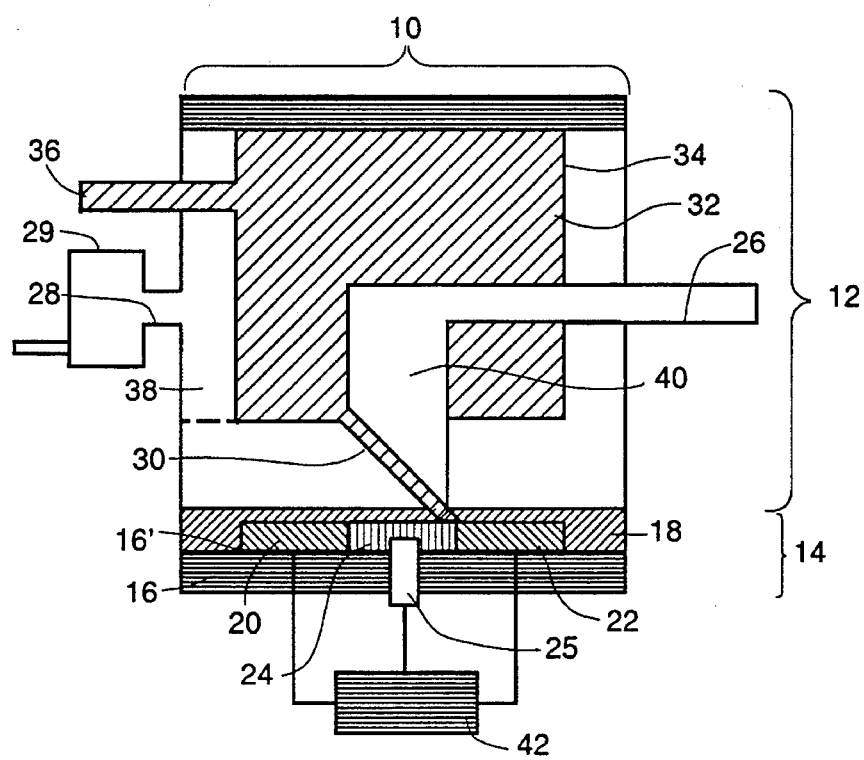
FIG. 1 is a cross-sectional view of the real-time toxic metals monitor cell of the present invention.

The present invention discloses an improved method for monitoring the presence of toxic metals in workplace air and a suitable monitoring device. Referring now to FIG. 1, a monitor cell 10 in accordance with the present invention comprises a base 12 and a removable assembly 14.

The removable assembly 14 comprises a flat, electrically insulating substrate 16 having a top surface 16' and an electrolyte cell 18 having an anode 20 and a cathode 22 both supported on the substrate and laterally spaced apart to define a controlled volume 24. The bottom surface of the anode 20 and the bottom surface of the cathode 22 are both supported by the top surface 16' of the flat substrate 16; the controlled volume 24 is defined by the lateral area spacing between the anode 20 and the cathode 22 and by the thickness of the two electrodes. A reference electrode 25 is mounted in the electrolyte cell between the anode 20 and the cathode 22. An electronic potentiostat 42 is connected to the anode 20, the cathode 22, and the reference electrode 25.

The base 12 has an air inlet 26 for admitting the air to be sampled, an air outlet 28 connected to a personnel air sampling pump 29, a wick 30 for conveying electrolyte 32 stored in a electrolyte reservoir 34 having a filler inlet 36, an exhaust air plenum 38 connected to the air outlet 28, and a channel 40 having two ends, one end connected to the air inlet and the other end connected to the air outlet. Personnel air sampling pumps are well-known and readily available, and any of such pumps may be employed in the practice of the invention. As shown in FIG. 1, the channel 40 is shown having an L-shaped configuration, although the invention is not so limited.

The wick 30 is positioned between a portion of the channel 40 and the electrolyte cell 18. The wick 30 is in contact with the exhaust air plenum 38 and is made permeable to air by incorporating a hydrophobic material such as polytetrafluoroethylene, available under the trade name TEFLON® from E.I. Du Pont de Nemours (Wilmington, Del.). The wick 30 comprises interlocking hydrophilic and hydrophobic pores to maximize contact between air and electrolyte streams. The structure is similar to that of electrochemical gas-diffusion electrodes which are fabricated by sintering together particles of polytetrafluoroethylene and a hydrophilic material such as carbon; this structure is disclosed by J. Giner, "The structure of hydrophobic gas diffusion electrodes", in *From Electrocatalysis to Fuel Cells*, G. Sandstede, Ed., University of Washington Press, Seattle, pp. 215–222 (1972). Once air has passed through the wick 30, it escapes via the exhaust plenum 38.

Figure 1A:
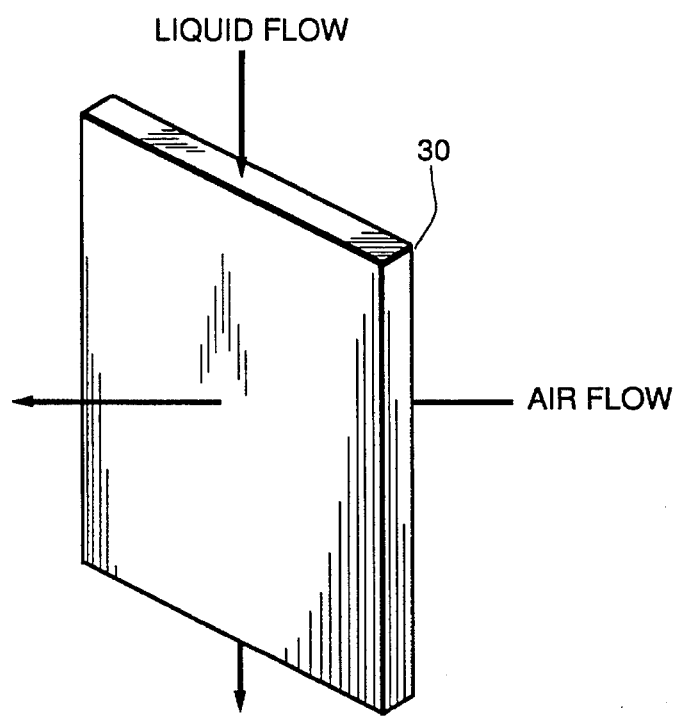
FIG. 1a is a perspective view of a portion of the monitor cell of FIG. 1, depicting the orthogonal flow paths of gas (sampled air) and liquid (electrolyte) to maximize the rate of dissolution of metal particles in the air in the electrolyte.

FIG. 1a depicts the use of orthogonal flow paths of gas (air) and liquid (electrolyte) through the wick 30 to maximize the rate at which metal particles in the air stream are dissolved in the electrolyte.

Although the following description of the present invention covers the detection of a particular toxic metal, cadmium, the present invention is not limited to any one toxic material. As previously defined the term toxic metals is used herein to include but is not limited to hazardous, inorganic species, such as cadmium, lead, mercury, and thallium and their soluble compounds. These compounds include any oxides, chlorides, acetates, nitrates, perchlorates, phosphates, and other salts that can be dissolved in water or in acidic solutions. Thus, the electrolyte cell 18 is generic since no electrolyte nor cathode and anode materials are specified.

For use in detecting these metals, the cathode may comprise iron or silver; the anode may comprise any dimensionally-stable, insoluble (non-consumable) metal or other electronic conductor, such as graphite, a noble metal (e.g., platinum, palladium, iridium), or a commercial anode material. An example of such commercial anode material is a noble metal oxide supported on a titanium substrate, available under the trade name DSA® from ELTECH Systems Corporation, Specialty Electrodes Group, Chardon, Ohio.

The electrolyte advantageously comprises an aqueous acidic solution that dissolves toxic metals. Examples of such acids are given in the following Table.

TABLE

Electrolytes for real-time toxic metals monitor.

| Acid | Formula | Approx. Conc.[1] | Metal | | | |
|---|---|---|---|---|---|---|
| | | | Cd | Pb | Hg | Tl |
| acetic | $CH_3COOH$ | 100% | Pref. | Pref. | Pref. | Pref. |
| nitric[2] | $HNO_3$ | 68% | Poss. | Poss. | Poss. | Poss. |
| perchloric[2] | $HClO_4$ | 74%[3] | Poss. | Poss. | — | Poss. |
| o-phosphoric | $H_3PO_4$ | 85% | Pref. | — | — | Poss. |
| sulfuric | $H_2SO_4$ | 40% | Pref. | — | Poss. | Pref. |

Notes:
Pref. = preferred; Poss. = possible.
[1]Steady-state concentration is determined by the humidity of the incoming air.
[2]Strong oxidizer; may limit choice of cell materials.
[3]Perchloric acid dihydrate.

In the preferred embodiment, ambient air, sampled from a point near the worker's mouth and nose, is drawn into the monitor cell 10. The electrolyte 32 flows by capillary action from the electrolyte reservoir 34 via a small opening, through the wick 30 into the electrolyte cell 18. The air sample is pumped through the air inlet 26 by the personnel air pump (not shown) into the first end of the channel 40, out of the second end of the channel 40 through the wick 30, and then out through the exhaust air plenum 38. A solution is then formed in the electrolyte cell 18 comprising the controlled volume 24 of electrolyte 32 and any toxic metal particles from the air sample. The potentiostat 42 controls the current between the anode 20 and the cathode 22 of the electrolyte cell 18 so as to maintain the cathode at some preset electrical potential versus the reference electrode 25. The preset electrical potential lies between 0.0 and −2.0 volts versus a saturated calomel reference electrode and is chosen to give a rate of hydrogen evolution at the cathode 22 equivalent to a current between $10^{-4}$ and 1 amp per square centimeter.

At least one catalytic site on the cathode 22 for the evolution of hydrogen is poisoned by an amount of at least one toxic metal atom which plates out of the solution in the electrolyte cell 18 onto the cathode 22. The amount of the toxic metal plating out of the solution onto the cathode 22 is monitored in real time by detecting a change in the current flow. A measure of the toxic metals is determined from the change in the current flow by comparing the measure to a safety standard for airborne levels of the toxic metals and generating a warning signal when the measure is at least equal to the level of the standard. The warning signal is then communicated to the personnel so that appropriate action may be taken.

The method is sensitive to very small levels of cadmium because catalytic sites for hydrogen evolution are completely poisoned by a single atomic layer of cadmium. For a typical catalytic electrode material, one square centimeter of surface area corresponds to about $2\times10^{-11}$ gram molecules. Thus, complete poisoning requires only about 0.2 micrograms of cadmium per square centimeter of electrode surface. Much smaller quantities will be detectable in practice. For example, if the current for hydrogen evolution started at 100 microamps per square centimeter, a decrease to 90 microamps would indicate the deposition of about 0.02 micrograms of cadmium per square centimeter. A short response time is achieved by using a small electrolyte volume. For example, the electrolyte volume is preferably in the range of about 0.1 to 10 milliliters. While one suitable electrolyte cell design is illustrated in FIG. 1, other suitable electrolyte cell designs will be readily apparent to those skilled in this art.

EXAMPLES

The operating principle of the method of the present invention was demonstrated using both iron and silver electrodes at two cadmium concentrations. Tests were run in a sealed beaker containing 600 milliliters of 1 normal sulfuric acid that was continuously purged with nitrogen. Electrode potentials were measured against a saturated calomel reference electrode (SCE). A rod of graphite was used as the anode. The iron electrode was prepared by sheathing a 0.5 centimeter diameter steel rod in heat-shrink polyolefin tubing. The end of the rod was polished on 600 grit emery paper prior to each test. The silver electrode was prepared by masking off a sheet of silver foil with platers' tape to expose an area of approximately 0.5 square centimeters. The exposed surface was abraded with 600 grit emery paper prior to testing. The electrolyte comprised sulfuric acid.

Using conventional electrochemical equipment, the rate of hydrogen evolution was recorded on each electrode as a function of potential. The currents at each potential stabilized within a few seconds and resulting curves of current versus potential were consistent with published data; see, e.g., S. Trasatti, "Development of the work function approach to the underpotential deposition of metals: application to the hydrogen evolution reaction", Zeitschrift für Physikalishe Chemie Neue Folge, Bd. 98, S. 75–94 (1975). The same current-potential behavior was recorded repeatedly over the course of several hours with no indication of long-term change in activity.

EXAMPLE 1

Figure 2:
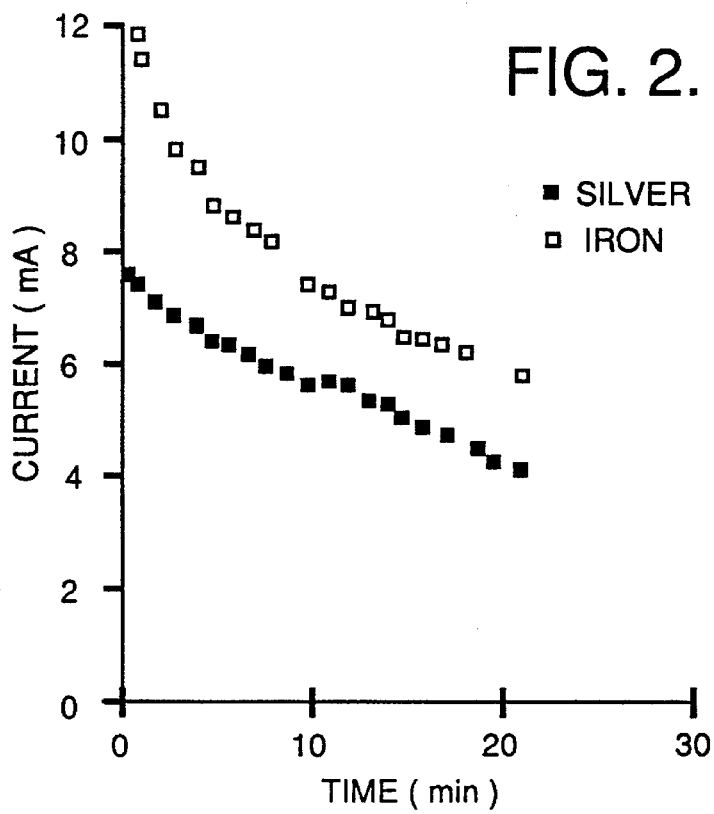
FIG. 2, on coordinates of current (milliamps) and time (minutes), is a plot illustrating the poisoning of hydrogen evolution on iron and silver electrodes by 0.4 parts per million cadmium.

The silver electrode was immersed in 1 Normal sulfuric acid and the potential was set at −1.0 volts versus SCE. This potential was selected to give a current of the order of 10 milliamps. When the current had stabilized, 1 milliliter of a dilute cadmium solution was added, yielding a calculated cadmium concentration of 0.4 parts per million. The resulting change in current with time is shown in FIG. 2. The linear region of current decay after about 5 minutes corresponded to a poisoning rate of about 2% per minute. This rate is consistent with the expected rate of cadmium diffusion to the electrode. The rapid initial decay indicates that cadmium deposition was not yet under diffusion control.

The iron electrode was then immersed in the same solution and the potential was set at −0.8 volts versus SCE, again giving a current of the order of 10 milliamps. The plot of current versus time is shown in FIG. 2. The results agreed closely with those observed on silver, yielding a poisoning rate of about 2% per minute.

EXAMPLE 2

Figure 3:
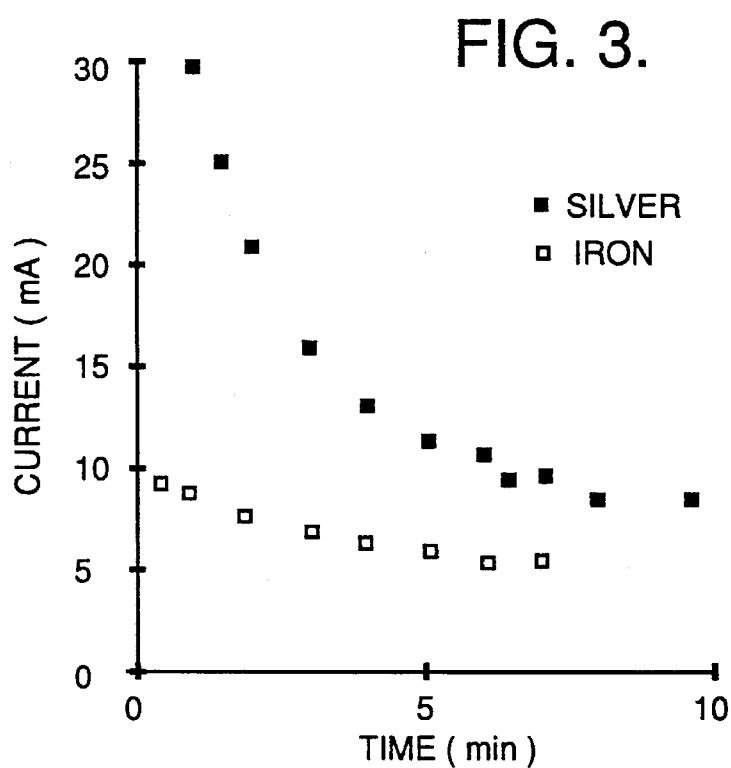
FIG. 3 is a plot similar to that of FIG. 2, but showing the poisoning of hydrogen evolution on iron and silver electrodes by 0.8 parts per million cadmium.

Cadmium was anodically dissolved off the surface of the silver electrode by switching the potential to 0.5 volts versus SCE. This treatment also etched the electrode, raising its effective surface area. As a result, the measured currents were several times larger than in Example 1. A second aliquot of cadmium solution was added to the test cell doubling the calculated concentration to 0.8 parts per million. The potential was immediately switched back to −1.0 volts. The resulting current-time trace is shown in FIG. 3. The linear region is less well defined but the decay rate was approximately 4% per minute, or double that in Example 1.

Cadmium deposited on the iron electrode in Example 1 was removed by taking the electrode out of solution and repolishing it. The electrode was then returned to the cell and a potential of −0.8 volts applied. The resulting current time trace is shown in FIG. 3. Agreement is again seen with the silver trace, indicating a decay rate in the linear region of about 4% per minute.

The equipment and methods described above can be used to detect airborne particles of several other metals. In particular, lead acts in exactly the same way as cadmium in poisoning hydrogen evolution at catalytic electrodes. For lead detection, perchloric acid or acetic acid would be preferred over sulfuric acid as the electrolyte because lead sulfate is insoluble.

Figure 4A:
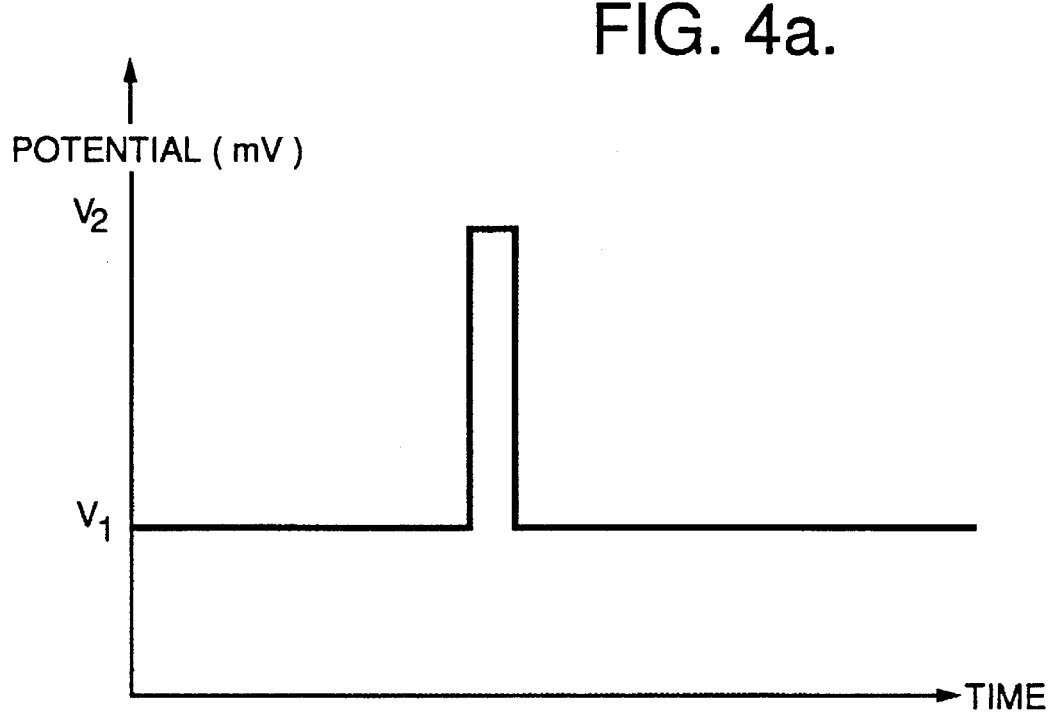
FIGS. 4a and 4b, on coordinates of potential (millivolts.
Figure 4B:
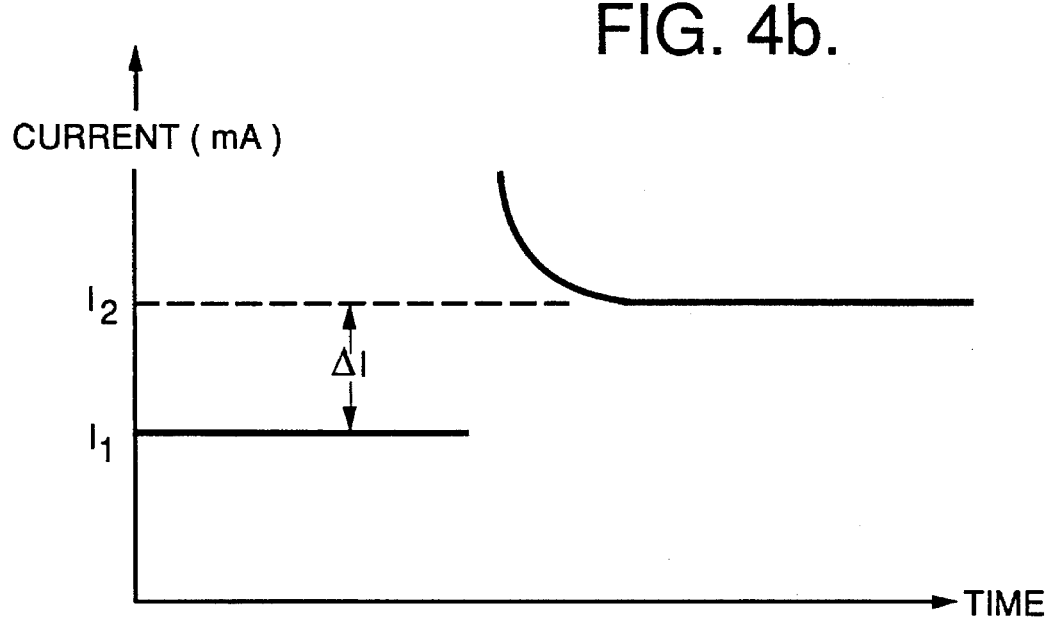

If lead and cadmium were both present, the sensor would yield a response in proportion to the sum of the two concentrations. Values of the individual metal concentrations could be extracted by modifying the sequence of voltage signals applied to the electrodes. For example, cadmium is 277 millivolts more active than lead, meaning that it will deplate or go back into solution at a less positive electrode potential. Referring to FIG. 4, one strategy would be to briefly shift the applied potential $V_1$ (where the hydrogen evolution current is $I_1$) to a more positive value, $V_2$ such that cadmium will redissolve but lead will remain on the surface. Upon returning the potential to $V_1$, the increase in hydrogen evolution current $\Delta I$ will indicate what portion of the surface was initially covered with cadmium. Any residual poisoning can then be attributed to lead. Calibration data obtained with known concentrations of cadmium and lead would then be used to determine actual levels of the two metals. Electrolytes such as acetic, perchloric, or nitric acids would be preferred over sulfuric acid for simultaneous lead and cadmium detection.

The examples show that sub parts per million concentrations of cadmium can readily be detected via its poisoning effect on catalytic electrodes. In the examples given, a cadmium concentration of only 0.4 parts per million was detected within a few minutes. A cell designed to maximize ionic diffusion should be able to detect ten times lower concentrations in a comparable time period. With these sensitivities, the present invention will be able to detect airborne cadmium particles at concentrations well below the permissible exposure threshold.

Thus, there has been disclosed an improved device for real-time monitoring of the presence of toxic metals in workplace air. It will be readily apparent to those of ordinary skill in this art that various changes and modifications of an obvious nature may be made, and all such changes and modifications are considered to fall within the scope of the invention, as defined by the appended claims.

What is claimed is:

1. A device for monitoring the concentration of toxic metals in workplace air, comprising a monitor cell comprising a base and a removable assembly, wherein (a) said removable assembly comprises (1) a flat, electrically insulating substrate having a first surface, (2) an electrolyte cell having an anode and a cathode disposed on said first surface, said anode and cathode spaced apart to define a controlled volume for holding a quantity of an electrolyte, and (3) means for applying a controlled electrical potential to said cathode of said electrolyte cell; and (b) said base comprises (1) an air inlet portion for sampling air, (2) an air outlet portion connected to an air sampling pump, (3) a channel connecting said air inlet and said air outlet and adapted to introduce said air to said electrolyte, (4) a reservoir for storing said electrolyte for said electrolyte cell, (5) wick means for supplying said electrolyte from said reservoir to said electrolyte cell and (6) wick means for providing contact between said air and said electrolyte in said channel whereby said toxic metals dissolve in said electrolyte.

2. The device of claim 1 wherein said toxic metals comprise at least one metal selected from the group consisting of cadmium, lead, mercury, and thallium.

3. The device of claim 1 wherein said cathode comprises a metal selected from the group consisting of iron and silver and said anode comprises a material selected from the group consisting of non-consumable metals, electronic conductors, noble metals, and noble metal oxides supported on metal substrates.

4. The device of claim 3 wherein said anode is selected from the group consisting of graphite, platinum, palladium, and iridium.

5. The device of claim 1 wherein said electrolyte comprises an aqueous acidic solution of an acid selected from the group consisting of acetic acid, nitric acid, perchloric acid, o-phosphoric acid, and sulfuric acid.

6. The device of claim 1 wherein said means for supplying said electrolyte and said means for providing contact between said air and said electrolyte are identical and comprise a wick material comprising interlocking hydrophilic and hydrophobic pores.

7. The device of claim 1 wherein said controlled electrical potential to said cathode ranges from 0 to about −2 volts versus a saturated calomel reference electrode.

8. The device of claim 1 wherein said controlled volume ranges from about 0.1 to 10 milliliters.

9. A method for monitoring the concentration of toxic metals in workplace air breathed by personnel comprising:

(a) obtaining a sample of said workplace air;

(b) providing a monitor cell comprising (1) an electrolyte cell having an anode and a cathode spaced apart a controlled volume filled with an electrolyte, (2) an electrolyte reservoir for storing said electrolyte and means for supplying said electrolyte to said electrolyte cell, and (3) means for applying a controlled electrical potential to said cathode of said electrolyte cell;

(c) forming a solution of any said toxic metals in said electrolyte;

(d) controlling said electrical potential of said cathode of said electrolyte cell such that hydrogen is evolved at said cathode at a current between about $10^{-4}$ and 1 amp per square centimeter;

(e) poisoning at least one catalytic site on said cathode for said evolution of hydrogen by an amount of at least one toxic metal atom plating out of said solution in said electrolyte cell onto said cathode;

(f) monitoring in real time said amount of said toxic metal plating out of said solution onto said cathode by detecting a change in said current flow;

(g) determining a measure of said toxic metals from said change in said current flow and comparing said measure to a safety standard for airborne levels of said toxic metals.

10. The method of claim 9, further comprising generating a warning signal when said measure is at least equal to the level of said standard.

11. The method of claim 10, further comprising communicating said warning signal to said personnel.

12. The method of claim 9 wherein said solution is formed by:

(a) flowing said electrolyte by capillary action from said electrolyte reservoir through a wick into said electrolyte cell; and (b) pumping said sample through said wick.

13. The method of claim 12 wherein said wick comprises interlocking hydrophilic and hydrophobic pores.

14. The method of claim 9 wherein said toxic metals comprise at least one metal selected from the group consisting of cadmium, lead, mercury, and thallium.

15. The method of claim 9 wherein said cathode comprises a metal selected from the group consisting of iron and silver and said anode comprises a material selected from the group consisting of non-consumable metals, electronic conductors, and noble metals.

16. The method of claim 15 wherein said anode is selected from the group consisting of graphite, platinum, palladium, and iridium.

17. The method of claim 9 wherein said electrolyte comprises an aqueous acidic solution of an acid selected from the group consisting of acetic acid, nitric acid, perchloric acid, o-phosphoric acid, and sulfuric acid.

18. The method of claim 9 wherein said controlled electrical potential ranges from about 0 to −2 volts versus a saturated calomel reference electrode.

19. The method of claim 9 wherein said controlled volume ranges from about 0.1 to 10 milliliters.

* * * * *